US012573116B2

(12) United States Patent
Zhang et al.

(10) Patent No.: US 12,573,116 B2
(45) Date of Patent: Mar. 10, 2026

(54) SYSTEMS AND METHODS FOR IMAGE PROCESSING

(71) Applicant: SHANGHAI UNITED IMAGING HEALTHCARE CO., LTD., Shanghai (CN)

(72) Inventors: Na Zhang, Shanghai (CN); Le Yang, Shanghai (CN); Yang Hu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 590 days.

(21) Appl. No.: 17/930,063

(22) Filed: Sep. 6, 2022

(65) Prior Publication Data

US 2023/0076352 A1      Mar. 9, 2023

(30) Foreign Application Priority Data

Sep. 7, 2021    (CN) .......................... 202111042761.X
Sep. 7, 2021    (CN) .......................... 202111043188.4

(51) Int. Cl.
*G06T 11/00*          (2006.01)
*A61B 6/02*           (2006.01)
*A61B 6/50*           (2024.01)

(52) U.S. Cl.
CPC ............ *G06T 11/008* (2013.01); *A61B 6/025* (2013.01); *A61B 6/502* (2013.01); *G06T 11/005* (2013.01);
(Continued)

(58) Field of Classification Search
CPC .... G06T 11/008; G06T 11/005; G06T 11/006; G06T 2210/41; G06T 3/40; G06T 15/20;
(Continued)

(56) References Cited

U.S. PATENT DOCUMENTS 9,449,403 B2      9/2016   Jerebko
2007/0183564 A1*  8/2007   Li ........................... A61B 6/465
                                                          378/22
(Continued)

FOREIGN PATENT DOCUMENTS

CN        105184835 A      12/2015
CN        107871332 A      4/2018
(Continued)

OTHER PUBLICATIONS

Ge, Jun et al., Digital Tomosynthesis Mammography: Improvement of Artifact Reduction Method for High-attenuation Objects on Reconstructed Slices, Proc. of SPIE, 2008, 6 pages.
(Continued)

*Primary Examiner* — Nimesh Patel
(74) *Attorney, Agent, or Firm* — METIS IP LLC

(57) ABSTRACT

The present disclosure provides a system and method for image processing. The method may include obtaining multiple projection images of a subject acquired by an imaging device from multiple view angles; generating an initial slice image of the subject by image reconstruction based on the multiple projection images; determining, based on the multiple projection images, a target out-of-plane artifact of the initial slice image; and generating a corrected slice image by correcting the initial slice image with respect to the target out-of-plane artifact.

20 Claims, 9 Drawing Sheets

300

(52) U.S. Cl.
CPC ........ *G06T 11/006* (2013.01); *G06T 2210/41* (2013.01)

(58) Field of Classification Search
CPC . G06T 2207/10012; G06T 2207/10052; G06T 3/20; G06T 3/60; G06T 5/80; G06T 2207/30101; G06T 7/0012; G06T 2207/10116; G06T 7/0004; G06T 2207/20221; G06T 7/75; G06T 2207/10081; G06T 2207/10132; G06T 5/50; G06T 2200/04; G06T 2207/10136; G06T 5/70; G06T 7/55; G06T 7/60; G06T 17/00; G06T 2207/10101; G06T 15/00; G06T 2207/20224; G06T 2207/20084; G06T 2211/404; A61B 6/025; A61B 6/502; A61B 6/5211; A61B 6/5258; A61B 8/483; A61B 5/055; A61B 6/5217; A61B 6/5247; A61B 6/504; A61B 8/12; A61B 8/5261; A61B 6/032; A61B 6/466; A61B 6/5223; A61B 6/5235; A61B 8/466; A61B 5/7267; A61B 8/5238
See application file for complete search history.

(56) References Cited

U.S. PATENT DOCUMENTS

| | | | | |
|---|---|---|---|---|
| 2008/0253635 | A1* | 10/2008 | Spies | G06T 11/008 |
| | | | | 382/131 |
| 2009/0087067 | A1* | 4/2009 | Khorasani | A61B 6/03 |
| | | | | 382/132 |
| 2014/0093029 | A1 | 4/2014 | Masumoto et al. | |
| 2014/0294138 | A1* | 10/2014 | Jerebko | A61B 6/025 |
| | | | | 378/4 |
| 2016/0300367 | A1* | 10/2016 | Nakanishi | G06T 11/005 |
| 2019/0221010 | A1* | 7/2019 | Fukuda | A61B 6/025 |
| 2019/0221013 | A1 | 7/2019 | Fukuda | |
| 2019/0259187 | A1* | 8/2019 | Heese | A61B 6/025 |
| 2020/0410727 | A1* | 12/2020 | Yamakawa | G06V 10/44 |
| 2021/0049810 | A1 | 2/2021 | Dennerlein | |
| 2021/0082095 | A1 | 3/2021 | Fukuda | |
| 2021/0125384 | A1* | 4/2021 | Lee | G06T 11/005 |
| 2021/0233215 | A1* | 7/2021 | Manhart | G06T 5/00 |
| 2023/0127935 | A1* | 4/2023 | Chen | A61B 8/5238 |
| | | | | 382/131 |

FOREIGN PATENT DOCUMENTS

| | | | |
|---|---|---|---|
| CN | 110458762 | A | 11/2019 |
| CN | 110473297 | A | 11/2019 |
| CN | 111986285 | A | 11/2020 |
| EP | 3232936 | B1 | 9/2019 |

OTHER PUBLICATIONS

First Office Action in Chinese Application No. 202111042761.X mailed on Apr. 26, 2025, 18 pages.

* cited by examiner

300

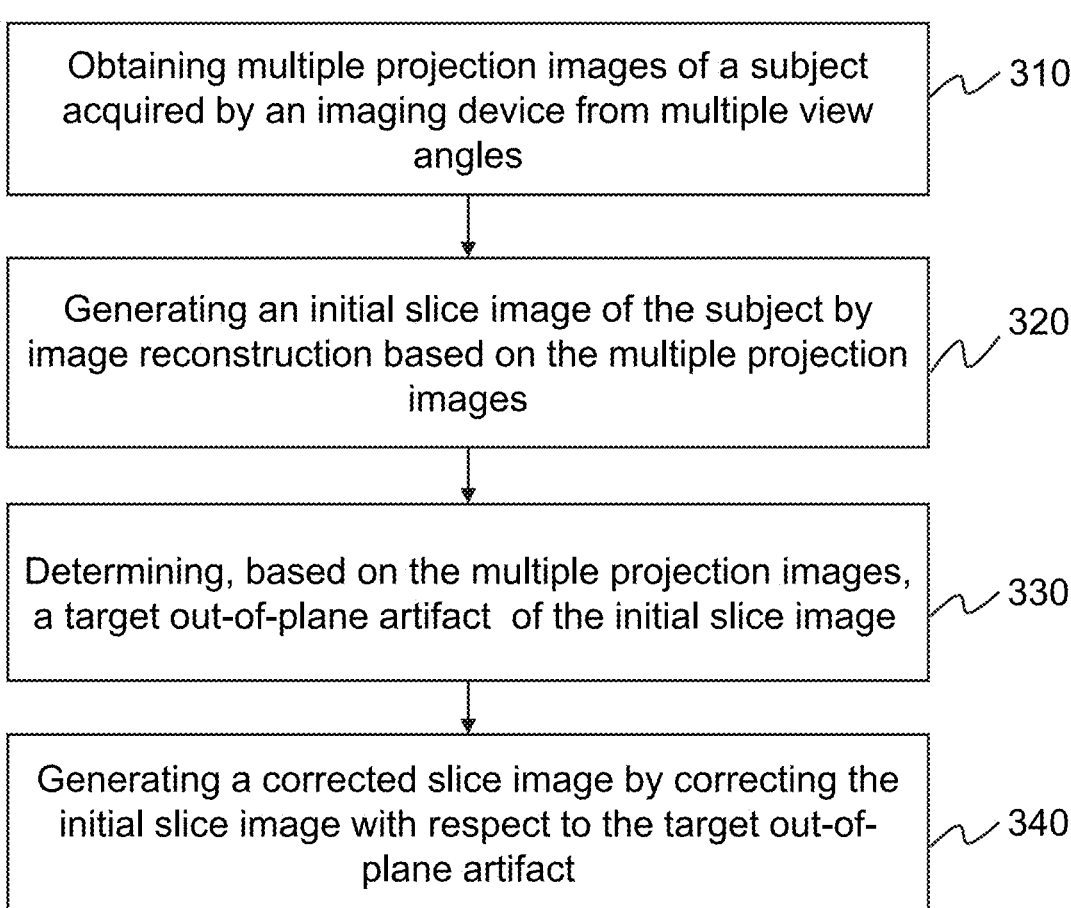

Obtaining multiple projection images of a subject acquired by an imaging device from multiple view angles ⟋310

Generating an initial slice image of the subject by image reconstruction based on the multiple projection images ⟋320

Determining, based on the multiple projection images, a target out-of-plane artifact of the initial slice image ⟋330

Generating a corrected slice image by correcting the initial slice image with respect to the target out-of-plane artifact ⟋340

FIG. 3

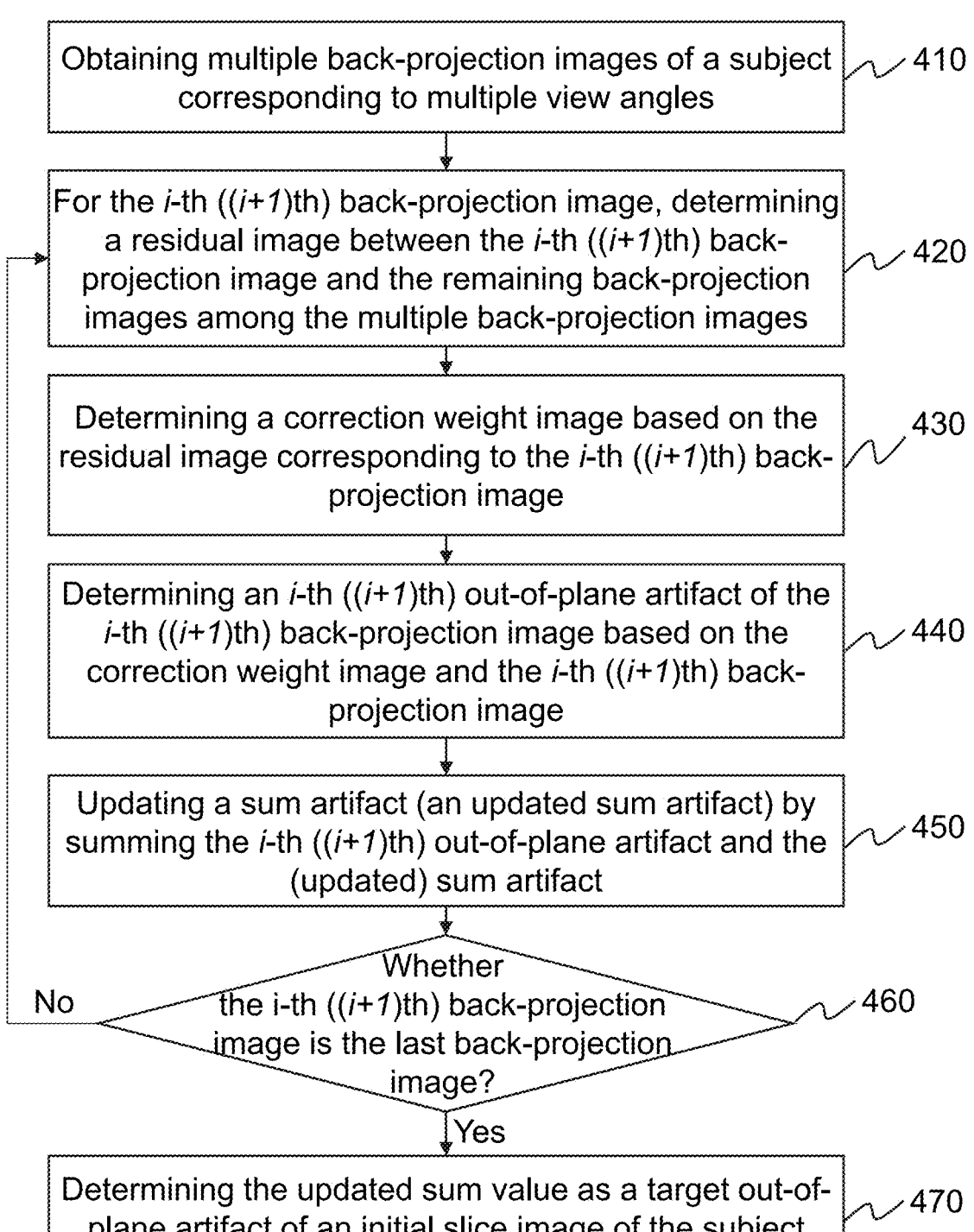

400

Obtaining multiple back-projection images of a subject corresponding to multiple view angles ~410

For the *i*-th (((*i*+1)th) back-projection image, determining a residual image between the *i*-th (((*i*+1)th) back-projection image and the remaining back-projection images among the multiple back-projection images ~420

Determining a correction weight image based on the residual image corresponding to the *i*-th (((*i*+1)th) back-projection image ~430

Determining an *i*-th (((*i*+1)th) out-of-plane artifact of the *i*-th (((*i*+1)th) back-projection image based on the correction weight image and the *i*-th (((*i*+1)th) back-projection image ~440

Updating a sum artifact (an updated sum artifact) by summing the *i*-th (((*i*+1)th) out-of-plane artifact and the (updated) sum artifact ~450

Whether the i-th (((*i*+1)th) back-projection image is the last back-projection image? ~460

No

Yes

Determining the updated sum value as a target out-of-plane artifact of an initial slice image of the subject ~470

FIG. 4

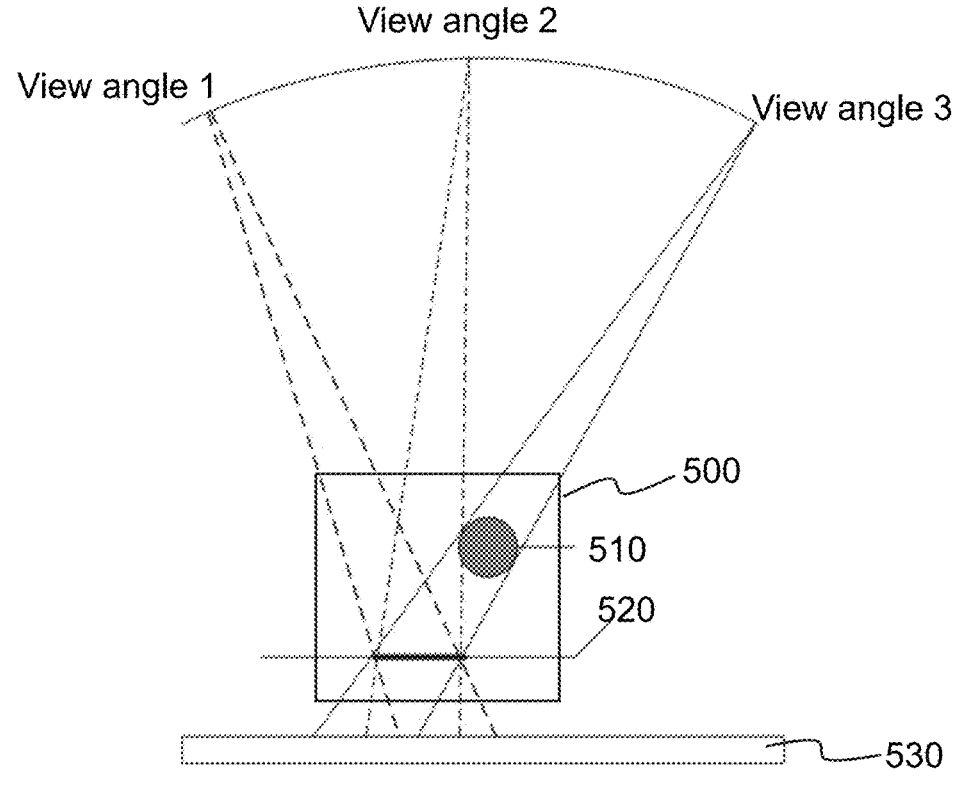
FIG. 5
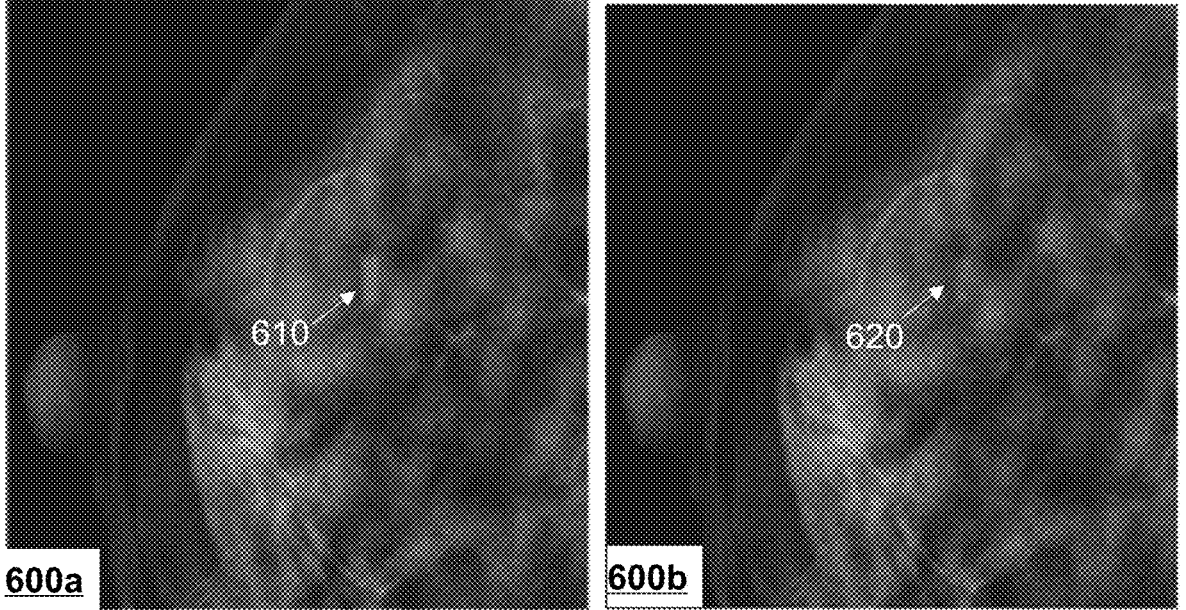
FIG. 6A                    FIG. 6B

800

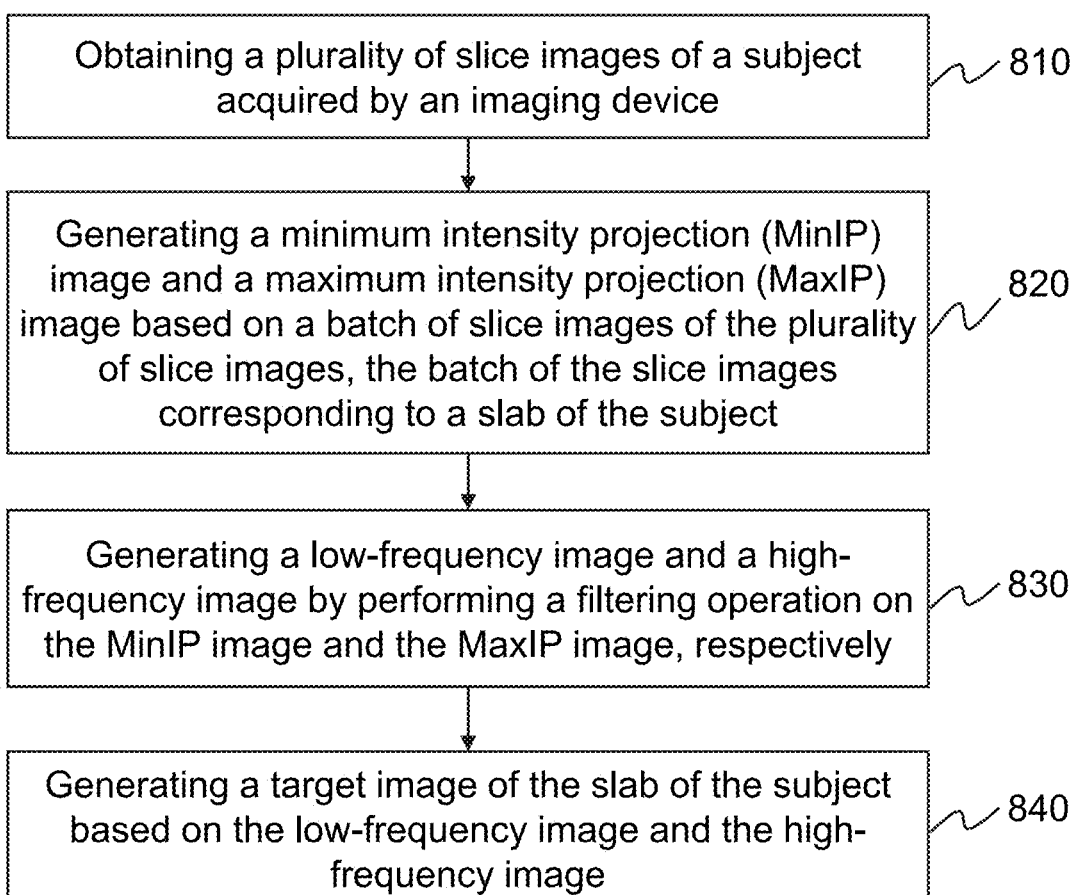

Obtaining a plurality of slice images of a subject acquired by an imaging device    810

Generating a minimum intensity projection (MinIP) image and a maximum intensity projection (MaxIP) image based on a batch of slice images of the plurality of slice images, the batch of the slice images corresponding to a slab of the subject    820

Generating a low-frequency image and a high-frequency image by performing a filtering operation on the MinIP image and the MaxIP image, respectively    830

Generating a target image of the slab of the subject based on the low-frequency image and the high-frequency image    840

FIG. 8

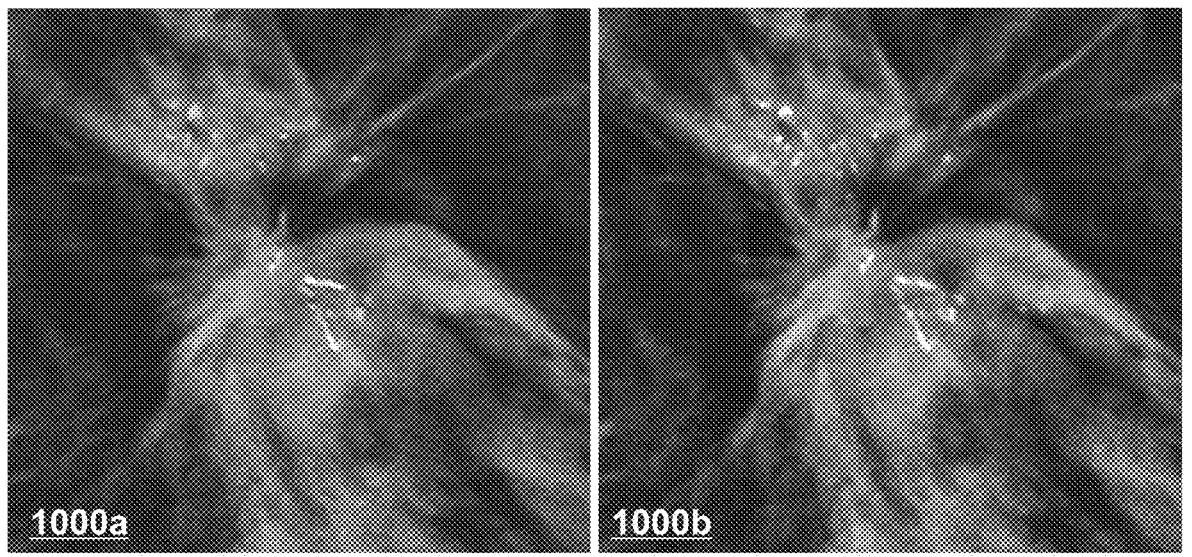
FIG. 10A                              FIG. 10B

SYSTEMS AND METHODS FOR IMAGE PROCESSING

CROSS-REFERENCE TO RELATED APPLICATIONS

This application claims priority of Chinese Patent Application No. 202111043188.4, filed on Sep. 7, 2021, and Chinese Patent Application No. 202111042761.X, filed on Sep. 7, 2021, the contents of each of which are hereby incorporated by reference.

TECHNICAL FIELD

The disclosure generally relates to imaging systems, and more particularly, relates to systems and methods for image processing.

BACKGROUND

Breast cancer is a common disease that seriously threatens women's health worldwide. A digital breast tomosynthesis (DBT) device can collect slice images of a breast, and thus enhances the likelihood of finding a lesion (e.g., a tumor) by removing overlapping breast tissue represented in different 2D slices of the breast. However, because of the limited angular range acquisition in a DBT device, the reconstructed slice images may have reduced resolution and may be affected by out-of-plane artifacts. In addition, in order to avoid missing a lesion in slice images, a small slice interval may be set during the slice image reconstruction process, which may result in the generation of a large number of slice images, thus increasing the amount of work for a user (e.g., a doctor) to make a diagnosis by reviewing the slice images and causing a great burden on storage of these slice images. Therefore, it is desirable to provide systems and methods for image processing to reduce an out-of-plane artifact in a slice image and reduce the amount of work for the user.

SUMMARY

According to an aspect of the present disclosure, a system for image processing is provided. The system may include at least one storage device storing a set of instructions, and at least one processor configured to communicate with the at least one storage device. When executing the executable instructions, the at least one processor may be configured to direct the system to perform one or more of the following operations. The system may obtain multiple projection images of a subject acquired by an imaging device from multiple view angles. The system may generate an initial slice image of the subject by image reconstruction based on the multiple projection images. The system may determine, based on the multiple projection images, a target out-of-plane artifact of the initial slice image. The system may generate a corrected slice image by correcting the initial slice image with respect to the target out-of-plane artifact.

In some embodiments, the system may generate, based on each of the multiple projection images, a back-projection image corresponding to the projection image using a back-projection algorithm.

In some embodiments, to generate, based on each of the multiple projection images, a back-projection image corresponding to the projection image, the system may perform a preprocessing operation on the projection image to generate a preprocessed image. The preprocessing operation may include at least one of a segmentation operation, a gray value transformation operation, a window width adjustment operation, or a window level adjustment operation. The system may generate, based on the preprocessed projection image, the back-projection image.

In some embodiments, to generate an initial slice image of the subject by image reconstruction based on the multiple projection images, the system may generate, based on the multiple back-projection images, the initial slice image.

In some embodiments, to determine, based on the multiple projection images, a target out-of-plane artifact of the initial slice image, the system may determine an out-of-plane artifact of each back-projection image of the multiple back-projection images and determine the target out-of-plane artifact based on the multiple out-of-plane artifacts of the multiple back-projection images.

In some embodiments, to determine an out-of-plane artifact of each back-projection image of the multiple back-projection images, the system may determine a residual image between the back-projection image and the remaining back-projection images among the multiple back-projection images, and determine, based on the residual image and the back-projection image, the out-of-plane artifact of the back-projection image.

In some embodiments, to determine a residual image between the back-projection image and the remaining back-projection images among the multiple back-projection images, the system may determine an average back-projection image of the remaining back-projection images among the multiple back-projection images; and determine the residual image by subtracting the back-projection image from the average back-projection image.

In some embodiments, to determine, based on the residual image and the back-projection image, the out-of-plane artifact of the back-projection image, the system may determine, based on a minimum pixel value of pixel values of the residual image corresponding to the back-projection image, a correction weight image; and determine, based on the correction weight image and the back-projection image, the out-of-plane artifact of the back-projection image.

In some embodiments, to determine the target out-of-plane artifact based on the multiple out-of-plane artifacts of the multiple back-projection images, the system may determine the target out-of-plane artifact by summing the multiple out-of-plane artifacts of the multiple back-projection images.

In some embodiments, to generate a corrected slice image by correcting the initial slice image with respect to the target out-of-plane artifact, the system may generate the corrected slice image by subtracting the target out-of-plane artifact from the initial slice image.

In some embodiments, the system may generate, based on the multiple projection images, a plurality of initial slice images of the subject, each of the plurality of initial slice images corresponding to a slice of the subject. The system may generate a plurality of corrected slice images by correcting the plurality of initial slice images with respect to a plurality of target out-of-plane artifacts. The system may generate, based on a batch of corrected slice images of the plurality of corrected slice images, a minimum intensity projection (MinIP) image and a maximum intensity projection (MaxIP) image, the batch of corrected slice images corresponding to a slab of the subject. The system may generate a low-frequency image and a high-frequency image by performing a filtering operation on the MinIP image and the MaxIP image, respectively. The system may generate, based on the low-frequency image and the high-frequency image, a target image of the slab of the subject.

In some embodiments, to determine, based on a batch of corrected slice images of the plurality of corrected slice images, a minimum intensity projection (MinIP) image and a maximum intensity projection (MaxIP) image, the system may generate the MinIP image by performing an MinIP operation on the batch of corrected slice images and generate the MaxIP image by performing an MaxIP operation on the batch of corrected slice images.

In some embodiments, to generate a low-frequency image and a high-frequency image by performing a filtering operation on the MinIP image and the MaxIP image, respectively, the system may determine the low-frequency image by performing a low-pass filtering operation on the MinIP image and determine the high-frequency image by performing a high-pass filtering operation on the MaxIP image.

In some embodiments, to generate, based on the low-frequency image and the high-frequency image, a target image of the subject, the system may generate an intermediate image by superimposing the low-frequency image and the high-frequency image; and generate, based on the intermediate image and the MaxIP image, the target image.

In some embodiments, to generate, based on the intermediate image and the MaxIP image, the target image, the system may determine a first weight for the intermediate image and a second weight for the MaxIP image. The system may generate the target image by determining a weighted sum of the intermediate image and the MaxIP image.

In some embodiments, the system may transmit the target image to a terminal device for display.

In some embodiments, the batch of corrected slice images may correspond to consecutive slices of the subject.

In some embodiments, the subject may include a breast. The imaging device may include a digital breast tomosynthesis (DBT) device.

According to another aspect of the present disclosure, a system for image processing is provided. The system may include at least one storage device storing a set of instructions, and at least one processor configured to communicate with the at least one storage device. When executing the executable instructions, the at least one processor may be configured to direct the system to perform one or more of the following operations. The system may obtain a plurality of slice images of a subject acquired by an imaging device. The system may generate, based on a batch of slice images of the plurality of slice images, a minimum intensity projection (MinIP) image and a maximum intensity projection (MaxIP) image. The batch of the slice images may correspond to a slab of the subject. The system may generate a low-frequency image and a high-frequency image by performing a filtering operation on the MinIP image and the MaxIP image, respectively. The system may generate, based on the low-frequency image and the high-frequency image, a target image of the slab of the subject.

According to yet an aspect of the present disclosure, a method for image processing is provided. The method may be implemented on a computing device having at least one processor and at least one storage device. The method may include obtaining multiple projection images of a subject acquired by an imaging device from multiple view angles; generating an initial slice image of the subject by image reconstruction based on the multiple projection images; determining, based on the multiple projection images, a target out-of-plane artifact of the initial slice image; and generating a corrected slice image by correcting the initial slice image with respect to the target out-of-plane artifact.

According to yet an aspect of the present disclosure, a method for image processing is provided. The method may be implemented on a computing device having at least one processor and at least one storage device. The method may include obtaining a plurality of slice images of a subject acquired by an imaging device; generating, based on a batch of slice images of the plurality of slice images, a minimum intensity projection (MinIP) image and a maximum intensity projection (MaxIP) image, the batch of the slice images corresponding to a slab of the subject; generating a low-frequency image and a high-frequency image by performing a filtering operation on the MinIP image and the MaxIP image, respectively; and generating, based on the low-frequency image and the high-frequency image, a target image of the slab of the subject.

According to yet an aspect of the present disclosure, a non-transitory computer readable medium is provided. The non-transitory computer readable medium may include at least one set of instructions for image processing. When executed by at least one processor of a computing device, the at least one set of instructions may direct the at least one processor to perform a method. The method may include obtaining multiple projection images of a subject acquired by an imaging device from multiple view angles; generating an initial slice image of the subject by image reconstruction based on the multiple projection images; determining, based on the multiple projection images, a target out-of-plane artifact of the initial slice image; and generating a corrected slice image by correcting the initial slice image with respect to the target out-of-plane artifact.

According to yet an aspect of the present disclosure, a non-transitory computer readable medium is provided. The non-transitory computer readable medium may include at least one set of instructions for image processing. When executed by at least one processor of a computing device, the at least one set of instructions may direct the at least one processor to perform a method. The method may include obtaining a plurality of slice images of a subject acquired by an imaging device; generating, based on a batch of slice images of the plurality of slice images, a minimum intensity projection (MinIP) image and a maximum intensity projection (MaxIP) image, the batch of the slice images corresponding to a slab of the subject; generating a low-frequency image and a high-frequency image by performing a filtering operation on the MinIP image and the MaxIP image, respectively; and generating, based on the low-frequency image and the high-frequency image, a target image of the slab of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 3 is a flowchart illustrating an exemplary process for image correction according to some embodiments of the present disclosure;

FIG. 4 is a flowchart illustrating an exemplary process for determining a target out-of-plane artifact of an initial slice image according to some embodiments of the present disclosure;

FIG. 5 is a schematic diagram illustrating an exemplary process for correcting an initial slice image according to some embodiments of the present disclosure;

FIG. 6A illustrates an exemplary slice image before image correction;

FIG. 6B illustrates an exemplary slice image after image correction according to some embodiments of the present disclosure;

FIG. 8 is a flowchart illustrating an exemplary process for image generation according to some embodiments of the present disclosure;

FIG. 10A illustrates an exemplary slice image of a subject; and

FIG. 10B illustrates an exemplary target image of a slab of a subject according to some embodiments of the present disclosure.

DETAILED DESCRIPTION

Figure 1:
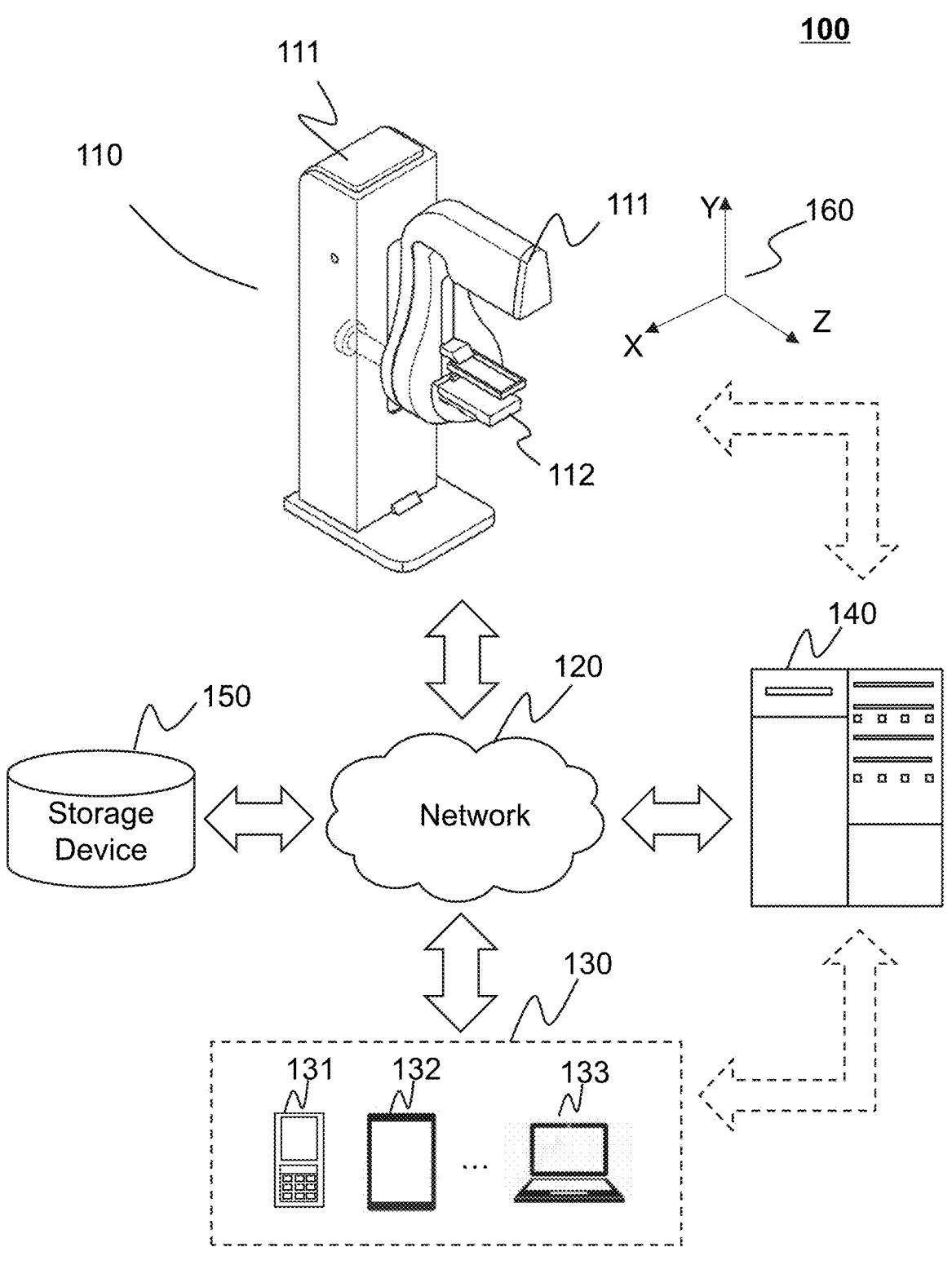
FIG. 1 is a schematic diagram illustrating an exemplary image processing system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

In the present disclosure, the term "image" may refer to a two-dimensional (2D) image, a three-dimensional (3D) image, or a four-dimensional (4D) image (e.g., a time series of 3D images). In some embodiments, the term "image" may refer to an image of a region (e.g., a region of interest (ROI)) of a subject. In some embodiment, the image may be a medical image, an optical image, etc.

In the present disclosure, a representation of a subject (e.g., a breast) in an image may be referred to as "subject" for brevity. Further, an image including a representation of the subject may be referred to as an image of the subject or an image including the subject for brevity. Still further, an operation performed on a representation of a subject in an image may be referred to as an operation performed on the subject for brevity. For instance, a segmentation of a portion of an image including a representation of a region of interest from the image may be referred to as a segmentation of the ROI for brevity.

An aspect of the present disclosure relates to systems and methods for image processing. For example, the systems may obtain multiple projection images of a subject acquired by an imaging device from multiple view angles. The systems may generate an initial slice image of the subject by image reconstruction based on the multiple projection images. The systems may determine a target out-of-plane artifact of the initial slice image based on the multiple projection images. The systems may generate a corrected slice image by correcting the initial slice image with respect to the target out-of-plane artifact. As another example, the systems may obtain a plurality of slice images of a subject acquired by an imaging device. The systems may generate a minimum intensity projection (MinIP) image and a maximum intensity projection (MaxIP) image based on a batch of slice images of the plurality of slice images. The batch of the slice images may correspond to a slab of the subject. The systems may generate a low-frequency image and a high-frequency image by performing a filtering operation on the MinIP image and the MaxIP image, respectively. The systems may further generate a target image of the slab of the subject based on the low-frequency image and the high-frequency image.

According to some embodiments of the present disclosure, the target out-of-plane artifact of the initial slice image may be determined based on the attenuation of a substance relative to its surrounding tissue. Further, the initial slice image can be directly corrected based on the target out-of-plane artifact of the initial slice image, thereby simplifying the image correction process and improving the efficiency and accuracy of the image correction. Moreover, there is no need to rely on other detection algorithms or statistical information in the projection images and/or back-projection images, which can not only further improve the accuracy of the image correction, but also improve the applicability of the image correction.

In some embodiments of the present disclosure, by performing one low-pass filtering operation on the generated MinIP image and one high-pass filtering operation on the generated MaxIP image, the low-frequency image and the high-frequency image used to generate the target image may be obtained, which reduces the count of filtering operations, thereby simplifying the image generation process, reducing imaging processing time, and improving the efficiency of image generation.

Additionally or alternatively, by generating a target image based on the MinIP image and the MaxIP image of each batch of the plurality of slice images, information regarding a lesion, a tissue, a contour profile, etc., represented in each batch of slice images may be preserved in the corresponding target image, thereby obviating the need to review each of the plurality of slice images for diagnosis, which in turn may reduce the amount of work involved in diagnosis.

FIG. 1 is a schematic diagram illustrating an exemplary image processing system according to some embodiments of the present disclosure. As illustrated in FIG. 1, the image processing system 100 may include an imaging device 110, a network 120, a terminal device 130, a processing device 140, and a storage device 150. The components in the image processing system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The imaging device 110 may be configured to scan a subject using radiation rays (e.g., X-rays, y-rays, a-rays, neutron, proton, etc.) and generate imaging data used to generate one or more images relating to the subject. The imaging data relating to at least one part of the subject may include an image (e.g., a slice image), projection data (e.g., a projection image), or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. Merely by way of example, the subject may include a patient, a man-made object, etc. As another example, the subject may include a specific portion, organ, and/or tissue of the patient. For example, the subject may include a breast, the liver, the heart, the stomach, the head, the brain, the neck, the body, a shoulder, an arm, the thorax, a blood vessel, a soft tissue, a knee, feet, or the like, or any combination thereof. In some embodiments, the imaging device 110 may include a computed tomography (CT) device, a computed tomography-positron emission tomography (CT-PET) scanner, a computed tomography-magnetic resonance imaging (CT-MRI) scanner, a digital radiography (DR) device, a digital breast tomosynthesis (DBT) device, a C-arm X-ray scanner, or the like, or a combination thereof. For illustration purposes, the DBT device may be taken as an exemplary imaging device 110 in the present disclosure.

In some embodiments, the imaging device 110 may include a gantry 111, one or more detectors 112, a radiation source 113, or any other components (e.g., a compression paddle, or a table). The gantry 111 may be configured to provide support for other components (e.g., the radiation source 113, the detector(s) 112, etc.) of the imaging device 110. In some embodiments, the detector(s) 112 and the radiation source 113 may be oppositely mounted on the gantry 111. In some embodiments, the gantry 111 may rotate and/or move. The radiation source 113 may rotate along with the gantry 111. A subject may be positioned in a detection region between the detectors 112 and the radiation source 113. The radiation source 113 may emit toward the subject radiation rays, and the detector(s) 112 may detect at least a portion of the radiation beams that have traversed through the subject within the detection region to generate projection data (or a projection image).

The network 120 may include any suitable network that can facilitate the exchange of information and/or data for the image processing system 100. In some embodiments, one or more components of the image processing system 100 (e.g., the imaging device 110, the terminal device 130, the processing device 140, the storage device 150) may communicate information and/or data with one or more other components of the image processing system 100 via the network 120. For example, the processing device 140 may obtain image data from the imaging device 110 via the network 120. As another example, the processing device 140 may obtain user instruction(s) from the terminal device 130 via the network 120. In some embodiments, the network 120 may be any type of wired or wireless network, or a combination thereof. In some embodiments, the network 120 may include one or more network access points. For example, the network 120 may include wired and/or wireless network access points such as base stations and/or internet exchange points through which one or more components of the image processing system 100 may be connected to the network 120 to exchange data and/or information.

The terminal device 130 may be connected to and/or communicate with the imaging device 110, the processing device 140, and/or the storage device 150. For example, the terminal device 130 may obtain a processed image from the processing device 140. As another example, the terminal device 130 may enable user interactions with the image processing system 100. In some embodiments, the terminal device 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal device 130 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to the processing device 140 via, for example, a bus, for further processing. Other types of input device may include a cursor control device, such as a mouse, a trackball, or cursor direction keys, etc. The output device may include a display, a speaker, a printer, or the like, or a combination thereof. In some embodiments, the terminal device 130 may be part of the processing device 140.

The processing device 140 may process data and/or information obtained from the imaging device 110, the terminal device 130, and/or the storage device 150. For example, the processing device 140 may determine a target out-of-plane artifact of an initial slice image and correct the initial slice image based on the target out-of-plane artifact. As another example, for a batch of slice images corresponding to a slab of a subject, the processing device 140 may generate a minimum intensity projection (MinIP) image and a maximum intensity projection (MaxIP) image based on the batch of slice images. The processing device 140 may generate a low-frequency image and a high-frequency image by performing a filtering operation on the MinIP image and the MaxIP image, respectively. The processing device 140 may generate a target image of the slab of the subject based on the low-frequency image and the high-frequency image. As a further example, the processing device 140 may transmit the target image to the terminal device 130 for display.

In some embodiments, the processing device 140 may be a computer, a user console, a single server or a server group, etc. The server group may be centralized or distributed. In some embodiments, the processing device 140 may be local or remote. For example, the processing device 140 may access information and/or data from the imaging device 110, the terminal device 130, and/or the storage device 150 via the network 120. As another example, the processing device 140 may be directly connected to the imaging device 110, the terminal device 130, and/or the storage device 150 to access information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device having a processor, a storage, an input/output (1/O), a communication port, etc. In some embodiments, the processing device 140 may be implemented on a processing circuit (e.g., a processor, a central processing unit (CPU)) of the terminal device 130.

The storage device 150 may store data, instructions, and/or any other information. In some embodiments, the storage device 150 may store data obtained from the terminal device 130 and/or the processing device 140. For example, the storage device 150 may store one or more images obtained from the processing device 140. In some embodiments, the storage device 150 may store data and/or instructions that the processing device 140 may execute or use to perform exemplary methods/systems described in the present disclosure. For example, the storage device 150 may store data and/or instructions that the processing device 140 may execute or use to correct a slice image having an out-of-plane artifact. In some embodiments, the storage device 150 may include a mass storage device, a removable storage device, a volatile read-and-write memory, a read-only memory (ROM), or the like, or any combination thereof. In some embodiments, the storage device 150 may be implemented on a cloud platform as described elsewhere in the disclosure.

In some embodiments, the storage device 150 may be connected to the network 120 to communicate with one or more other components of the image processing system 100 (e.g., the processing device 140, the terminal device 130, etc.). One or more components of the image processing system 100 may access the data or instructions stored in the storage device 150 via the network 120. In some embodiments, the storage device 150 may be part of the processing device 140.

The coordinate system 160 may include an X axis, a Y-axis, and a Z-axis. The X axis and the Z axis shown in FIG. 1 may be horizontal, and the Y-axis may be vertical. As illustrated, the positive X direction along the X axis may be from the right side to the left side of the imaging device 110 seen from the direction facing the front of the imaging device 110; the positive Y direction along the Y axis shown in FIG. 1 may be from the lower part to the upper part of the imaging device 110; the positive Z direction along the Z axis shown in FIG. 1 may refer to a direction in which the subject is moved out of the detection region of the imaging device 110 from the front of the imaging device 110.

It should be noted that the above description of the image processing system 100 is merely provided for the purposes of illustration, and not intended to limit the scope of the present disclosure. For persons having ordinary skills in the art, multiple variations and modifications may be made under the teachings of the present disclosure. For example, the assembly and/or function of the image processing system 100 may be varied or changed according to specific implementation scenarios. In some embodiments, the image processing system 100 may include one or more additional components (e.g., a storage device) and/or one or more components of the image processing system 100 described above may be omitted. Additionally or alternatively, two or more components of the image processing system 100 may be integrated into a single component. A component of the image processing system 100 may be implemented on two or more sub-components.

Figure 2:
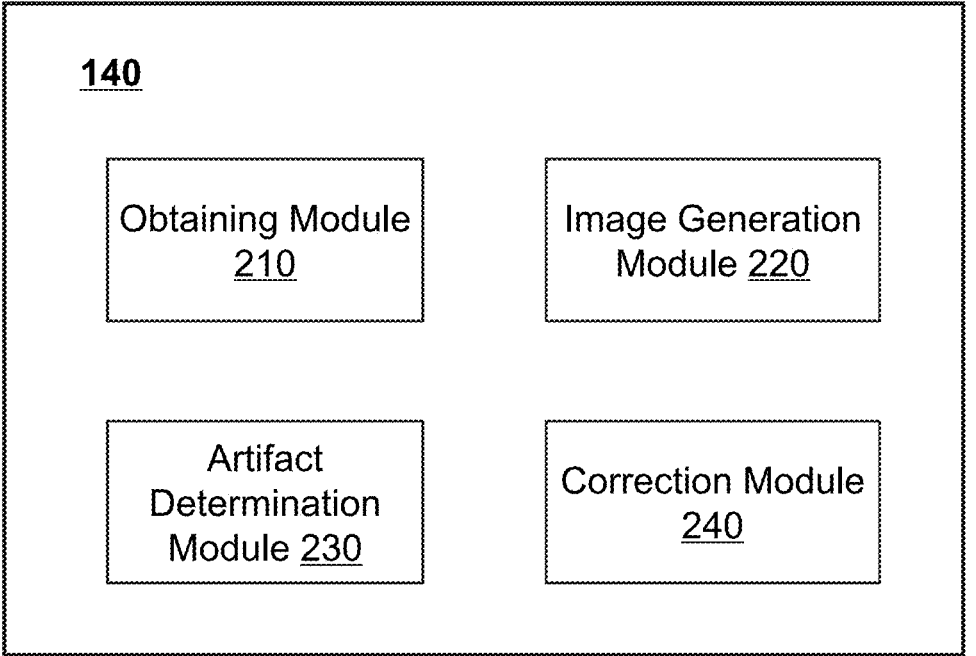
FIG. 2 is a block diagram illustrating exemplary processing device according to some embodiments of the present disclosure.

FIG. 2 is a block diagram illustrating exemplary processing device according to some embodiments of the present disclosure. As illustrated in FIG. 2, the processing device 140 may include an obtaining module 210, an image generation module 220, an artifact determination module 230, and a correction module 240. The modules may be hardware circuits of all or part of the processing device 140. The modules may also be implemented as an application or set of instructions read and executed by the processing device 140. Further, the modules may be any combination of the hardware circuits and the application/instructions. For example, the modules may be part of the processing device 140 when the processing device 140 is executing the application/set of instructions.

The obtaining module 210 may be configured to obtain multiple projection images of a subject acquired by an imaging device from multiple view angles.

The image generation module 220 may be configured to generate an initial slice image of the subject by image reconstruction based on the multiple projection images.

The artifact determination module 230 may be configured to determine a target out-of-plane artifact of the initial slice image based on the multiple projection images.

The correction module 240 may be configured to generate a corrected slice image by correcting the initial slice image with respect to the target out-of-plane artifact. More descriptions regarding the generation of the corrected slice image may be found elsewhere in the present disclosure (e.g., FIG. 3 and FIG. 4 and the descriptions thereof).

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, a module mentioned above may be divided into two or more units. For example, the image generation module 220 may be divided into two units, one of which may be configured to generate a back-projection image corresponding to a projection image, and the other one may be configured to generate the initial slice image. In some embodiments, the processing device 140 may include one or more additional modules, such as a storage module (not shown) for storing data.

FIG. 3 is a flowchart illustrating an exemplary process for image correction according to some embodiments of the present disclosure. In some embodiments, a process 300 may be implemented as a set of instructions (e.g., an application) stored in a storage device (e.g., the storage device 150). The processing device 140 (e.g., implemented on one or more modules illustrated in FIG. 2) may execute the set of instructions, and when executing the instructions, the processing device 140 may be configured to perform the process 300. The operations of the illustrated process 300 presented below are intended to be illustrative. In some embodiments, the process 300 may be accomplished with one or more additional operations not described, and/or without one or more of the operations discussed. Additionally, the order of the operations of the process 300 illustrated in FIG. 3 and described below is not intended to be limiting.

In 310, the processing device 140 (e.g., the obtaining module 210) may obtain multiple projection images of a subject acquired by an imaging device from multiple view angles. The subject may be biological or non-biological. For example, the subject may include a patient, a man-made object, etc., as described elsewhere in the present disclosure (e.g., FIG. 1 and the descriptions thereof).

The imaging device may scan the subject (e.g., a breast) from the multiple view angles using radiation rays (e.g., X-rays, y-rays, a-rays, neutron, proton, etc.) and generate the multiple projection images. Each view angle may correspond to one projection image. For example, as shown in FIG. 5, a radiation source of the imaging device may scan the subject 500 including a lesion 510 from view angle 1, view angle 2, and view angle 3. In some embodiments, the imaging device may include a CT device, a DBT device, etc., as described elsewhere in the present disclosure. See, e.g., FIG. 1 and relevant description thereof.

In some embodiments, the multiple projection images may be obtained from the imaging device (e.g., the imaging device 110) directly. In some embodiments, the multiple projection images may be obtained from the storage device 150. For example, the imaging device 110 may transmit acquired projection images to the storage device 150 for storage. The processing device 140 may obtain the multiple projection images from the storage device 150.

In some embodiments, the multiple projection images may include 2D projection images, 3D projection images, etc. In some embodiments, each projection image may include a plurality of pixels or voxels with pixel/voxel values or characteristics, e.g., luminance values, gray values, colors (or RGB values), saturation values, etc. A pixel in one projection image may correspond to one pixel in each of the other projection image. As used herein, two corresponding pixels (or voxels) in the two images may correspond to a same physical portion or position of the subject.

In some embodiments, in order to improve the image quality (e.g., contrast, clarity) of subsequently images (e.g., a back-projection image, an initial slice image, etc.) generated based on the multiple projection images, the processing device 140 may perform a preprocessing operation on each of the multiple projection images to generate a preprocessed image. In some embodiments, the preprocessing operation may include a filtering operation, a segmentation operation, a gray value transformation operation, a window width adjustment operation, a window level adjustment operation, or the like, or any combination thereof.

The filtering operation may eliminate image noises produced due to, e.g., sensors, circuitries, etc., of the imaging device. In some embodiments, the image noises may include a random variation of brightness or color information in the projection image.

The segmentation operation may segment a region of interest (ROI, e.g., a breast of a patient) from the projection image. In some embodiments, the segmentation operation may include using a segmentation algorithm, a segmentation model, etc. Exemplary segmentation algorithms may include a threshold-based segmentation algorithm, a compression-based algorithm, an edge detection algorithm, a machine learning-based segmentation algorithm, etc. The segmentation model may be a trained machine learning model. The training may be performed based on a plurality of groups of training data. Each group of training data may include a sample projection image and a corresponding training label (e.g., an ROI image, a segmentation mask). The processing device 140 may input the projection image into the segmentation model to determine the ROI image corresponding to the projection image. Exemplary segmentation models may include a convolutional neural network (CNN) model, a deep CNN (DCNN) model, a fully convolutional network (FCN) model, a recurrent neural network (RNN) model, etc.

The gray value transformation operation may transform pixel values (e.g., gray values) of pixels of the projection image (or the ROI image) based on a gray value transformation function to improve the contrast or image clarity of the projection image (or the ROI image). For example, the processing device 140 may transform the pixel values of pixels of the projection image according to a predetermined transformation relationship to generate a transformed image, thereby improving the image clarity of the projection image.

The window width adjustment operation and/or the window level adjustment operation may determine characteristic display parameter(s) (e.g., a window width, a window level) for the projection image (or the ROI image). In some embodiments, the window width and/or the window level for displaying the projection image (or the ROI image) may not need to be adjusted repeatedly, which may improve the efficiency of an operator for observing the projection image (or the ROI image).

In 320, the processing device 140 (e.g., the image generation module 220) may generate an initial slice image of the subject by image reconstruction based on the multiple projection images.

As used herein, a slice image refers to an image representation of a slice of the subject at a slice location. For instance, a slice image may include a representation of the subject at a slice location in a transverse plane of the subject that is parallel to an X-Y plane defined by the coordinate system 160 as illustrated in FIG. 1. In some embodiments, the processing device 140 may generate a plurality of slice images corresponding to a plurality of slice locations of the subject based on the multiple projection images according to a preset slice interval. The slice locations of the plurality of slice images may be in parallel planes. The initial slice image may be any slice image among the plurality of slice images. In the present disclosure, the initial slice image may be an image representation of a slice of the subject at an initial slice location of the subject. The initial slice location may be located at any position of the subject.

In some embodiments, for each of the multiple projection images, the processing device 140 may generate a back-projection image at the initial slice location using a back-projection algorithm based on the projection image. Specifically, the back-projection image may be generated based on one or more acquisition parameters associated with the imaging device according to the back-projection algorithm. Exemplary acquisition parameters may include a rotation radius of a radiation source (e.g., an X-ray tube), a source image receptor distance (SID), a source object distance (SOD), a view angle corresponding to the projection image, or the like. In some embodiments, the back-projection algorithm may include a direct back-projection algorithm, a filtered back-projection algorithm, etc.

The processing device 140 may generate the initial slice image based on the multiple back-projection images. For example, the processing device 140 may sum the multiple back-projection images to generate the initial slice image. As another example, the processing device 140 may determine a weighted sum on the multiple back-projection images to generate the initial slice image. It should be noted that in the present disclosure, a mathematical operation (e.g., addition, subtraction, multiplication, division, etc.) between two images may refer to the mathematical operation between pixel values of corresponding pixels in the two images. For example, summing the multiple back-projection images may refer to summing pixel values of corresponding pixels of the multiple projection images and a summed image may be obtained. A pixel value of a pixel in the summed image may be equal to a sum of pixel values of the corresponding pixels in the multiple back-projection images.

In 330, the processing device 140 (e.g., the artifact determination module 230) may determine a target out-of-plane artifact of the initial slice image based on the multiple projection images.

As used herein, the target out-of-plane artifact refers to an image of one or more substances outside the initial slice location at the initial slice location. In some embodiments, the substance(s) may include a dense tissue (e.g., a calcified lesion, a tumor, etc.) a large mass substance (e.g., an implant, a metal, etc.), or any other substance with a large attenuation coefficient.

In some embodiments, the target out-of-plane artifact may be determined based on multiple out-of-plane artifacts of the multiple back-projection images. For example, the processing device 140 may sum the multiple out-of-plane artifacts to generate the target out-of-plane artifact. As another example, the multiple out-of-plane artifacts may be weighted and summed to determine the target out-of-plane artifact.

In some embodiments, the out-of-plane artifact of each back-projection image may be determined based on a residual image between the back-projection image and the remaining back-projection images among the multiple back-projection images. The processing device 140 may determine the out-of-plane artifact of the back-projection image based on the residual image and the back-projection image. More descriptions regarding the determination of the out-of-plane artifact of the back-projection image may be found elsewhere in the present disclosure (e.g., FIG. 4 and the descriptions thereof). In some embodiments, the processing device 140 may determine the out-of-plane artifact of each back-projection image based on an artifact determination model. In some embodiments, the artifact determination model may be a trained machine learning model. For example, the processing device 140, or another processing device of the image processing system 100 or external to the image processing system 100, may train the artifact determination model using a plurality of training samples determined according to the process 400 or any other out-of-plane artifact determination techniques. The processing device 140 may input the back-projection image (or the corresponding projection image and the initial slice location) into the artifact determination model to determine the out-of-plane artifact corresponding to the back-projection image.

In some embodiments, the target out-of-plane artifact of the initial slice image may be determined based on a target artifact determination model. The target artifact determination model may be a trained machine learning model. For instance, the target artifact determination model may be trained based on a plurality of groups of training data. Each group of training data may include a sample initial slice image (or multiple sample projection images and a sample slice location) and a corresponding sample target out-of-plane artifact. The processing device 140 may input the initial slice image (or the multiple projection images and a slice location) into the target artifact determination model to determine the target out-of-plane artifact corresponding to initial slice image. In some embodiments, the target artifact determination model may include a convolutional neural network (CNN) model, a deep CNN (DCNN) model, a fully convolutional network (FCN) model, a recurrent neural network (RNN) model, or the like, or any combination thereof.

In 340, the processing device 140 (e.g., the correction module 240) may generate a corrected slice image by correcting the initial slice image with respect to the target out-of-plane artifact.

In some embodiments, the processing device 140 may generate the corrected slice image by subtracting the target out-of-plane artifact from the initial slice image. In some embodiments, the processing device 140 may further correct the target out-of-plane artifact based on a predetermined correction coefficient, and then correct the initial slice image using the corrected target out-of-plane artifact.

In some embodiments, the processing device 140 may transmit the corrected slice image to the terminal device 130 for display.

According to some embodiments of the present disclosure, the initial slice image can be directly corrected based on the target out-of-plane artifact of the initial slice image, thereby simplifying the image correction process and improving the efficiency and accuracy of the image correction.

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the models (e.g., the target artifact determination model, the segmentation model, etc.) used in the present disclosure may be obtained from one or more components of the image processing system 100 or an external source via a network. For example, the target artifact determination model may be previously trained by the processing device 140 or another computing device (e.g., a processing device of a vendor of the target artifact determination model), and stored in the storage device 150. The processing device 140 may access the storage device 150 and retrieve the target artifact determination model.

FIG. 4 is a flowchart illustrating an exemplary process for determining a target out-of-plane artifact of an initial slice image according to some embodiments of the present disclosure. In some embodiments, a process 400 may be implemented as a set of instructions (e.g., an application) stored in a storage device (e.g., the storage device 150). The processing device 140 (e.g., implemented on one or more modules illustrated in FIG. 2) may execute the set of instructions, and when executing the instructions, the processing device 140 may be configured to perform the process 400. The operations of the illustrated process 400 presented below are intended to be illustrative. In some embodiments, the process 400 may be accomplished with one or more additional operations not described, and/or without one or more of the operations discussed. Additionally, the order of the operations of the process 400 illustrated in FIG. 4 and described below is not intended to be limiting.

In some embodiments, one or more operations of the process 400 may be performed to achieve at least part of operation 330 as described in connection with FIG. 3. For example, the target out-of-plane artifact determined in 330 may be determined according to the process 400.

In 410, the processing device 140 (e.g., the obtaining module 210) may obtain multiple back-projection images of a subject corresponding to multiple view angles.

The multiple back-projection images may correspond to an initial slice location of the subject. The multiple back-projection images may be generated in a manner similar to that described in operation 320. In some embodiments, the processing device 140 may generate an initial slice image at the initial slice location based on the multiple back-projection images.

In 420, for the i-th back-projection image, the processing device 140 (e.g., the artifact determination module 230) may determine a residual image between the i-th back-projection image and the remaining back-projection images among the multiple back-projection images.

The i-th back-projection image may be any one of the multiple back-projection images. i may an integer greater than one. If the count or number of the back-projection images is N, wherein N is an integer greater than two, i may be an integer greater than one but less than or equal to N. The remaining back-projection images corresponding to the i-th back-projection image may be back-projection images in the multiple back-projection images except the i-th back-projection image. That is, the remaining back-projection images may be the first, the second, . . . , (i−1)th, (i+1)th, . . . , N-th back-projection images.

In some embodiments, the processing device 140 may regularly (e.g., based on the view angles) or irregularly (e.g., randomly) arrange the multiple back-projection images. The processing device 140 determine the i-th back-projection image based on the arranged back-projection images. For example, if the (i−1)th back-projection image is the 6-th back-projection, the i-th back-projection image may be the 7-th back-projection image.

In some embodiments, the processing device 140 may determine an average back-projection image of the remaining back-projection images among the multiple back-projection images. The processing device 140 may determine the residual image by subtracting the i-th back-projection image from the average back-projection image. For example, the residual image may be determined according to Equation (1) as follows:

$$\Delta i = \frac{slice_{Total} - slice_i}{N - 1} - slice_i,$$  (1)

where $\Delta i$ denotes the residual image corresponding to the i-th back-projection image, N denotes a total count of the multiple back-projection images, $slice_{Total}$ denotes a sum of the multiple back-projection images (i.e., the initial slice image), and $slice_i$ denotes the i-th back-projection image. Thus, ($slice_{Total}$-$slice_i$) may denote a sum of the remaining back-projection images corresponding to the i-th back-projection image;

$$\frac{slice_{Total} - slice_i}{N - 1}$$

may denote an average image of the remaining back-projection image corresponding to the i-th back-projection image.

Accordingly, a pixel value of a pixel in the residual image with respect to the i-th back-projection image may indicate a difference between pixels values of a corresponding pixel in the i-th back-projection image and a corresponding pixel in the average image of the remaining back-projection image. The pixel value of a pixel of the residual image may be a positive value, a negative value, or zero. A positive pixel value of a pixel of the residual image corresponding to the i-th back-projection image may indicate that the pixel value of the corresponding pixel in the average image of the remaining back-projection images is higher than the pixel value of the corresponding pixel in the i-th back-projection image. A negative pixel value of a pixel of the residual image corresponding to the i-th back-projection image may indicate that the pixel value of the corresponding pixel in the average image of the remaining back-projection images is lower than the pixel value of the corresponding pixel in the i-th back-projection image. A zero pixel value of a pixel of the residual image corresponding to the i-th back-projection image may indicate that the pixel value of the corresponding pixel in the average image of the remaining back-projection images is the same as the pixel value of the corresponding pixel in the i-th back-projection image. Merely by way of example, for an out-of-plane artifact due to the presence of a calcified lesion in the subject, if impacted by the out-of-plane artifact, a pixel in the i-th back-projection image may have a high pixel value, while the corresponding pixels in the remaining back-projection images may have a relative low pixel value, and therefore the pixel value of the corresponding pixel in the residual image may be negative. Accordingly, a small pixel value (e.g., a negative pixel value whose absolute value is large) of a pixel in the residual image may indicate that the difference between pixels values of a corresponding pixel in the i-th back-projection image and a corresponding pixel in the average image of the remaining back-projection image is large, which in turn may indicate that the pixel value of the corresponding pixel in the i-th back-projection image may be impacted by an out-of-plane artifact, and needs to be corrected.

In some embodiments, the processing device 140 may determine a candidate residual image between the i-th back-projection image and each of the remaining back-projection images by subtracting the i-th back-projection image from each of the remaining back-projection images. The processing device 140 may determine an average image of the candidate residual images as the residual image.

In some embodiments, the processing device 140 may divide the remaining back-projection images into several groups of back-projection images. For each group of back-projection images, the processing device 140 may determine a candidate residual image between the i-th back-projection image and the group of back-projection images in a similar manner as above mentioned. The processing device 140 may determine an average image of the several candidate residual images as the residual image. Accordingly, in some embodiments, the processing device 140 may process the groups of back-projection images in parallel to obtain the candidate residual images, and then determine the residual image by averaging the candidate residual images, thereby improving the speed of image processing.

In 430, the processing device 140 (e.g., the artifact determination module 230) may determine a correction weight image based on the residual image.

The correction weight image may be configured to correct the i-th back-projection image. Pixel values (e.g., gray values) of pixels of the correction weight image may be in a range from 0 to 1. The correction weight image may be configured such that the closer the pixel value at a position of the correction weight image is to 1, the greater the possibility that the position includes an impact by an out-of-plane artifact and that the closer the pixel value at a position of the correction weight image is to 0, the less likely the position includes an impact by an out-of-plane artifact (that is, the greater the possibility that the position includes true tissue information of the subject). Thus, an i-th out-ofplane artifact of the i-th back-projection image may be determined in operation 440 using the correction weight image.

In some embodiments, the correction weight image may relate to a correction coefficient. The correction coefficient may be a value in a range from 0 to 1 and the correction coefficient may not equal to 1. The correction coefficient may be configured to adjust a correction area of the i-th back-projection image that needs to be corrected. Merely by way of example, the correction coefficient may be configured such that the greater the correction coefficient is, the smaller the correction area of the i-th back-projection image may be. In some embodiments, the correction coefficient may be set according to a default setting of the image processing system 100 or preset by a user or operator (e.g., a doctor) via the terminal device 130. In some embodiments, the correction coefficient may be determined according to actual needs. For example, the correction coefficient may be determined according to a desired correction accuracy. The higher the desired correction accuracy is, the greater the correction coefficient may be, and the smaller the correction area of the i-th back-projection image may be.

Merely by way of example, the processing device 140 may identify the minimum pixel value (e.g., a negative pixel value whose absolute value is the highest) of pixels of the residual image. The processing device 140 may determine a first corrected residual image based on the minimum pixel value of pixel values of the residual image and the correction coefficient. For example, the processing device 140 may determine the first corrected residual image according to Equation (2) as follows:

$$\Delta i' = \Delta i - \alpha * Value_{min}, \tag{2}$$

where $\Delta i'$ denotes the first corrected residual image, $\alpha$ denotes the correction coefficient, and $Value_{min}$ denotes the minimum pixel value of pixel values (e.g., gray values) of the residual image $\Delta i$. Pixels whose pixel values are greater than 0 in the first corrected residual image may indicate that their corresponding positions are considered to be impacted by no or little out-of-plane artifact. If a is set to be 0, the residual image $\Delta i$ is the same as the first corrected residual image $\Delta i'$, and pixel(s) in the residual image $\Delta i$ having negative pixel value(s) is/are considered to be impacted by an out-of-plane artifact that need(s) to be corrected. If $\alpha$ is set to be a positive value below 1, a portion of the pixel(s) in the residual image $\Delta i$ having negative pixel value(s) has/have a negative pixel value in the first corrected residual image $\Delta i'$ and is/are considered to be impacted by an out-of-plane artifact that need(s) to be corrected.

Merely by way of example, for a set to be a positive value below 1, the processing device 140 may assign pixel values of pixels whose pixel values are greater than zero in the first corrected residual image to zero to generate a second corrected residual image. In such cases, a portion of pixels in the second corrected residual image may have pixel values of zero, while the remaining portion of pixels in the second corrected residual image have pixel values of less than zero. The pixels with pixel values less than zero may indicate that the corresponding positions may be subsequently corrected. In some embodiments, the smaller the pixel value (e.g., a negative pixel value whose absolute value is larger) of a pixel of the second corrected residual image is, the higher impact on a corresponding pixel in the i-th back-projection image by an out-of-plane artifact may be, and therefore a stronger correction of the pixel value of the corresponding pixel in the i-th back-projection image may be performed.

In some embodiments, the correction weight image may relate to the extent by which the pixel value of each pixel in the i-th back-projection image is corrected. Merely by way of example, the pixel value of each pixel of the correction weight image may (e.g., negatively) relate to the pixel value of a corresponding pixel in the second corrected residual image. Accordingly, the processing device 140 may determine the correction weight image based on the second corrected residual image. Merely by way of example, the processing device 140 may determine a third corrected residual image by inverting the second corrected residual image. For example, the processing device 140 may determine the third corrected residual image according to Equation (3) as follows:

$$\Delta i''' = -\Delta i'', \tag{3}$$

where $\Delta i''$ denotes the second corrected residual image and $\Delta i'''$ denotes the third corrected residual image. The processing device 140 may identity a maximum pixel value of pixel values of the third corrected residual image. The processing device 140 may determine the correction weight image according to Equation (4) as follows:

$$\omega_i = \frac{\Delta i'''}{Value_{max}}, \tag{4}$$

where $\omega_i$ denotes the correction weight image corresponding to the i-th back-projection image, and $Value_{max}$ denotes the maximum pixel value of pixel values of the third corrected residual image $\Delta i'''$.

In 440, the processing device 140 (e.g., the artifact determination module 230) may determine an i-th out-of-plane artifact of the i-th back-projection image based on the correction weight image and the i-th back-projection image.

Merely by way of example, the processing device 140 may determine the i-th out-of-plane artifact in the i-th back-projection image by multiplying the correction weight image and the i-th back-projection image.

In 450, the processing device 140 (e.g., the artifact determination module 230) may update a sum artifact by summing the i-th out-of-plane artifact and the sum artifact.

In some embodiments, before executing the process 400, the processing device 140 may initialize the sum artifact as zero. That is, each pixel value of pixels of the initial sum artifact is zero. Thus, for the first back-projection image, the updated sum artifact may be the same as the first out-of-plane artifact. The processing device 140 may update the sum artifact according to Equation (5) as follows:

$$Artifact_{updated} = Artifact_{sum} + Artifact_i, \tag{5}$$

Where $Artifact_{updated}$ denotes the updated sum artifact, $Artifact_{sum}$ denotes the sum artifact, and $Artifact_i$ denotes the i-th out-of-plane artifact. The $Artifact_{sum}$ may be equal to a sum of the already determined out-of-plane artifacts (e.g., the 1st out-of-plane artifact through the (i−1)-th out-of-plane artifact). In other words, the $Artifact_{sum}$ may be determined according to Equation (6) as follows:

$$Artifact_{sum} = Artifact_1 + Artifact_2 + \ldots + Artifact_{i-1}. \tag{6}$$

As a result, the $Artifact_{updated}$ may be determined as Equation (7) as follows:

$$Artifact_{updated} = Artifact_1 + Artifact_2 + \ldots + Artifact_{i-1} + Artifact_i. \tag{7}$$

In 460, the processing device 140 (e.g., the artifact determination module 230) may determine whether the i-th back-projection image is the last back-projection image among the N arranged back-projection images.

In response to determining that the i-th back-projection image is the last back-projection image of the arranged back-projection images, the processing device 140 may determine the updated sum artifact as a target out-of-plane artifact of the initial slice image of the subject in operation 470. On the other hand, in response to determining that the i-th back-projection image is not the last back-projection image, the processing device 140 may repeat operation 420 through 460 to determine a residual image corresponding to the (i+1)th back-projection image. In other words, the processing device 140 may store the updated sum artifact, for example, in the storage device 150, and replace the i-th back-projection image with the (i+1)th back-projection image and repeat operations 420-460. The processing device 140 may determine a correction weight image based on a minimum pixel value of pixel values of the residual image corresponding to the (i+1)th back-projection image. The processing device 140 may determine an (i+1)th out-of-plane artifact of the (i+1)th back-projection image based on the correction weight image and the (i+1)th back-projection image. The processing device 140 may update the updated sum artifact by summing the (i+1)th out-of-plane artifact and the updated sum artifact previously determined and determine whether the (i+1)th back-projection image is the last back-projection image.

In some embodiments, the processing device 140 may correct the initial slice image with respect to the target out-of-plane artifact. For example, the target out-of-plane artifact may be determined according to Equation (8) as follows:

$$\text{Slice}_{Correct}=\text{Slice}_{total}-\text{Artifact}_{total}, \tag{8}$$

where $\text{Slice}_{Correct}$ denotes the corrected slice image, $\text{Slice}_{total}$ denotes the initial slice image, and $\text{Artifact}_{total}$ denotes the target out-of-plane artifact.

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 430 and operation 440 may be combined into a single operation. As another example, one or more other optional operations (e.g., a storing operation) may be added elsewhere in the process 400. In the storing operation, the processing device 140 may store information and/or data (e.g., the multiple back-projection images, the updated sum artifact, etc.) associated with the image processing system 100 in a storage device (e.g., the storage device 150) disclosed elsewhere in the present disclosure.

FIG. 5 is a schematic diagram illustrating an exemplary process for correcting an initial slice image according to some embodiments of the present disclosure. As shown in FIG. 5, a subject 500 may include a calcified lesion 510 which has a large attenuation coefficient. The subject 500 may be scanned by a radiation source of an imaging device from view angle 1, view angle 2, and view angle 3, and the corresponding projection images 1, 2, and 3 may be obtained using a detector 530. The processing device 140 may generate three back-projection images at a slice location 520 based on the three projection images using a back-projection algorithm. Further, the processing device 140 may generate an initial slice image at the slice location 520 based on the three back-projection images.

Since radiation rays from view angle 3 passes through the calcified lesion 510, calcification information may be left on the slice location 520 during the back-projection reconstruction process. Pixel values of pixels relating to the calcification information may be relatively large (e.g., the bold black line shown in FIG. 5). In other words, the back-projection image 3 may include an out-of-plane artifact. On the contrary, radiation rays from view angle 1 and view angle 2 do not pass through the calcified lesion 510, and pixel values of pixels of the back-projection image 1 and the back-projection image 2 may be relatively small.

Thus, for the back-projection image 3, pixel values of a residual image between the back-projection image 3 and the remaining back-projection images (including the back-projection images 1 and 2) may be relatively low, i.e., negative pixel values whose absolute values are relatively large. The out-of-plane artifact corresponding to the back-projection image 3 may be extracted based on the residual image in a manner similar to that described in process 400 and determined as a target out-of-plane artifact of the initial slice image. The processing device 140 may correct the initial slice image by subtracting the target out-of-plane artifact from the initial slice image.

FIG. 6A illustrates an exemplary slice image before image correction. FIG. 6B illustrates an exemplary slice image after image correction according to some embodiments of the present disclosure. As shown in FIGS. 6A and 6B, before the image correction, slice image 600a included an evident out-of-plane artifact 610. After the image correction, the out-of-plane artifact 610 in slice image 600a was greatly reduced. Out-of-plane artifact 610 evident in FIG. 6A was substantially invisible at the corresponding position 620 in FIG. 6B.

Figure 7:
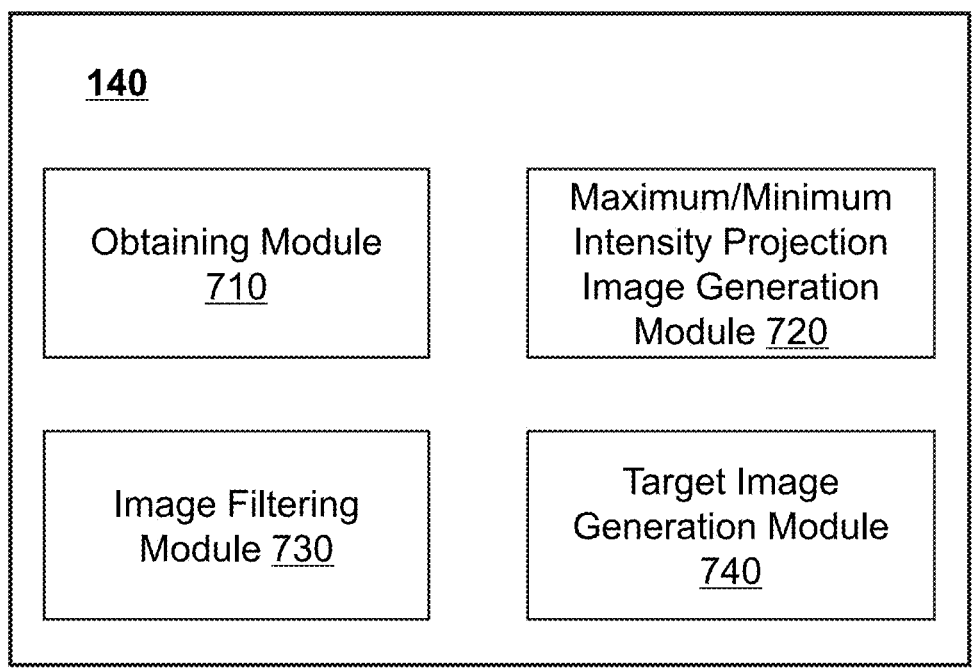
FIG. 7 is a block diagram illustrating exemplary processing device according to some embodiments of the present disclosure.

FIG. 7 is a block diagram illustrating exemplary processing device according to some embodiments of the present disclosure. As illustrated in FIG. 7, the processing device 140 may include an obtaining module 710, a maximum/minimum intensity projection image generation module 720, an image filtering module 730, and a target image generation module 740. The modules may be hardware circuits of all or part of the processing device 140. The modules may also be implemented as an application or set of instructions read and executed by the processing device 140. Further, the modules may be any combination of the hardware circuits and the application/instructions. For example, the modules may be part of the processing device 140 when the processing device 140 is executing the application/set of instructions.

The obtaining module 710 may be configured to obtain a plurality of slice images of a subject acquired by an imaging device.

The maximum/minimum intensity projection image generation module 720 may be configured to generate a minimum intensity projection (MinIP) image and a maximum intensity projection (MaxIP) image based on a batch of slice images of the plurality of slice images. The batch of the slice images may correspond to a slab of the subject.

The image filtering module 730 may be configured to generate a low-frequency image and a high-frequency image by performing a filtering operation on the MinIP image and the MaxIP image, respectively.

The target image generation module 740 may be configured to generate a target image of the slab of the subject based on the low-frequency image and the high-frequency image. More descriptions regarding the generation of the target image may be found elsewhere in the present disclosure (e.g., FIG. 8 and the descriptions thereof).

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the obtaining module 710 and the obtaining module 210 may be integrated into one module. In some embodiments, a module mentioned above may be divided into two or more units. For example, the maximum/minimum intensity projection image generation module 720 may be divided into two units, one of which may be configured to generate a maximum intensity projection image, and the other one may be configured to generate a minimum intensity projection image. In some embodiments, the processing device 140 may include one or more additional modules, such as a storage module (not shown) for storing data.

FIG. 8 is a flowchart illustrating an exemplary process for image generation according to some embodiments of the present disclosure. In some embodiments, a process 800 may be implemented as a set of instructions (e.g., an application) stored in a storage device (e.g., the storage device 150). The processing device 140 (e.g., implemented on one or more modules illustrated in FIG. 7) may execute the set of instructions, and when executing the instructions, the processing device 140 may be configured to perform the process 800. The operations of the illustrated process 800 presented below are intended to be illustrative. In some embodiments, the process 800 may be accomplished with one or more additional operations not described, and/or without one or more of the operations discussed. Additionally, the order of the operations of the process 800 illustrated in FIG. 8 and described below is not intended to be limiting.

In 810, the processing device 140 (e.g., the obtaining module 710) may obtain a plurality of slice images of a subject acquired by an imaging device.

In some embodiments, the imaging device (e.g., a DBT device) may scan the subject (e.g., a breast of a patient) from multiple view angles using radiation rays (e.g., X-rays, y-rays, a-rays, neutron, proton, etc.) and generate multiple projection images. Each view angle may correspond to one projection image. The processing device 140 may determine the plurality of slice images based on the multiple projection images and a slice interval according to an image reconstruction algorithm. Each of the plurality of slice images may correspond to a slice of the subject. The slice interval may affect a count or number of the plurality of slice images that correspond to (e.g., by providing a representation of) the subject, or a portion thereof. The greater the slice interval is, the fewer the slice images may be generated that correspond to the subject, or a same portion thereof. For example, the subject may be a breast of a patient. Assuming the thickness of the breast tissue is 50 mm, if the slice interval is 1 mm, 50 slice images may be generated. The 50 slice images may correspond to consecutive slices of the subject. Each slice image may correspond to a slice of the breast having a thickness of 1 mm. For the same breast tissue of 50 mm, if the slice interval is 5 mm, 10 slice images may be generated, each of which correspond to a slice of the breast having a thickness of 5 mm. In some embodiments, the slice interval may be set according to a default setting of the image processing system 100 or preset by a user or operator (e.g., a doctor) via the terminal device 130. In some embodiments, the image reconstruction algorithms may include an iterative reconstruction algorithm (e.g., a statistical reconstruction algorithm), a Fourier slice theorem algorithm, a filtered back-projection (FBP) algorithm, a fan-beam reconstruction algorithm, an analytic reconstruction algorithm, or the like, or any combination thereof.

In some embodiments, the plurality of slice images may be corrected to generate a plurality of corrected slice images. For example, the plurality of slice images may be corrected with respect to a plurality of target out-of-plane artifacts corresponding to the plurality of slice images. More descriptions about the correcting the slice images with respect to an out-of-plane artifact may be found elsewhere in the present disclosure (e.g., FIGS. 3 and 4 and the descriptions thereof).

In 820, the processing device 140 (e.g., the maximum/minimum intensity projection image generation module 720) may generate a minimum intensity projection (MinIP) image and a maximum intensity projection (MaxIP) image based on a batch of slice images of the plurality of slice images. The batch of the slice images may correspond to a slab of the subject. In some embodiments, the batch of slice images may correspond to consecutive slices of the subject.

The MinIP image may include image information of substances having a small attenuation coefficient (also be referred to as a low attenuation substance), such as a soft tissue of the subject. The image information of the low attenuation substance(s) may be reflected as low-frequency information of the MinIP image. Correspondingly, the MaxIP image may include image information of substances having a large attenuation coefficient (also be referred to as a high attenuation substance), such as a bone, a lesion, a metal implant, etc. The image information of the high attenuation substance(s) may be reflected as high-frequency information of the MaxIP image. The MaxIP image may also include a contour of the subject.

In some embodiments, the processing device 140 may generate the MinIP image by performing an MinIP operation on the batch of slice images. Specifically, the MinIP operation may be performed on the batch of slice images (including data of a 3D volume) in a certain direction, and the MinIP image may be obtained. The MinIP(s) may be generated based on element(s) having a minimum intensity (or density) along each projection ray directed to the subject's target site. That is, if the projection ray passes through the batch of slice images of the subject, the element(s) with the lowest intensity (or density) in the slice image(s) along the projection ray may be retained and projected onto a two-dimensional plane (e.g., a coronal plane, a sagittal plane, a transverse plane, etc.), thereby forming the MinIP image of the batch of the slice images. Thus, a pixel value of any pixel of the MinIP image may be a minimum value of pixel values of the corresponding pixels of the batch of slice images along a projection ray. As a result, by performing the MinIP operation, image information of the low attenuation substance(s) in the slab of the subject may be extracted.

Similarly, the processing device 140 may generate the MaxIP image by performing an MaxIP operation on the batch of slice images. Specifically, the MaxIP operation may be performed on the batch of slice images (including data of the 3D volume) in the certain direction, and the MaxIP image may be obtained. The MaxIP(s) may be generated based on element(s) having a maximum intensity (or density) along each projection ray directed to the subject's target site. That is, if the projection ray passes through the batch of slice images of the subject, the element(s) with the highest intensity (or density) in the slice image(s) along the projection ray may be retained and projected onto the two-dimensional plane, thereby forming the MaxIP image of the batch of the slice images. Thus, a pixel value of any pixel of the MaxIP image may be a maximum value of pixel values of the corresponding pixels of the batch of slice images along the projection ray. As a result, by performing the MaxIP operation, image information of the high attenuation substance(s) in the slab of the subject may be extracted.

In some embodiments, the MinIP image and/or the MaxIP image may be generated based on a corresponding trained machine learning model. The training process of the corresponding model may be not specifically limited or described in detail in the embodiments of the present disclosure.

In 830, the processing device 140 (e.g., the image filtering module 730) may generate a low-frequency image and a high-frequency image by performing a filtering operation on the MinIP image and the MaxIP image, respectively.

By performing the filtering operation, image noises in the MinIP image and the MaxIP image may be filtered out or reduced.

In some embodiments, the processing device 140 may determine the low-frequency image by performing a low-pass filtering operation on the MinIP image. The low-frequency image may be smoother and clearer than the MinIP image. In some embodiments, the low-pass filtering operation may be executed by a low-pass filter such as a Gaussian low-pass filter, a Butterworth low-pass filter, a Chebyshev low-pass filter, a mean low-pass filter, a median low-pass filter, a non-linear bilateral low-pass filter, etc.

Similarly, the processing device 140 may determine the high-frequency image by performing a high-pass filtering operation on the MaxIP image. The high-frequency image may be smoother and clearer than the MaxIP image. In some embodiments, the high-pass filtering operation may be executed by a high-pass filter such as a Canny filter, a Sobel filter, etc. It should be noted that the low-pass or high-pass filter may also be any other suitable low-pass or high-pass filter.

In 840, the processing device 140 (e.g., the target image generation module 740) may generate a target image of the slab of the subject based on the low-frequency image and the high-frequency image.

In some embodiments, the processing device 140 may generate an intermediate image by summing the low-frequency image and the high-frequency image. For example, the processing device 140 may determine the intermediate image according to Equation (9) as follows:

$$img1 = MinIPSynLow + MaxIPSynHigh, \qquad (9)$$

where img1 denotes the intermediate image, MinIPSynLow denotes the low-frequency image, and MaxIPSynHigh denotes the high-frequency image.

The processing device 140 may generate the target image of the slab of the subject based on the intermediate image. For example, the processing device 140 may directly designate the intermediate image as the target image. As another example, the processing device 140 may generate the target image by determining a weighted sum of the intermediate image and the MaxIP image. Specifically, the processing device 140 may determine a first weight for the intermediate image and a second weight for the MaxIP image. For example, the processing device 140 may determine the target image according to Equation (10) as follows:

$$Img = \varphi_1 * img1 + \varphi_2 * MaxIPSyn, \qquad (10)$$

where Img denotes the target image of the slab of the subject, $\varphi_1$ denotes the first weight, $\varphi_2$ denotes the second weight, and MaxIPSyn denotes the MaxIP image.

A sum of the first weight and the second weight may be equal to 1. The greater the first weight that is associated with the intermediate image, the more evident the morphology of the low attenuation substance(s) (e.g., soft tissues) of the subject in the target image. On the contrary, the greater the second weight that is associated with the MaxIP image, the more evident the high attenuation substance(s) (e.g., a lesion) of the subject in the target image. In some embodiments, the first weight and/or the second weight may be set according to a default setting of the image processing system 100 or preset by a user or operator (e.g., a doctor) via the terminal device 130. For example, in the case where a lesion in the target image needs to be illustrated, a relatively small first weight and a relatively large second weight may be employed. As another example, in the case where the integrity of the target image needs to be improved, that is, the morphological information of the subject needs to be displayed, a relatively large first weight and a relatively small second weight may be set. In some embodiments, a user may adjust the first weight and/or the second weight based on a desired effect to be illustrated in the target image. For example, the processing device 140 may transmit the target image to a terminal device for display. The user may review the target image and adjust the first weight and/or the second weight through a user interface shown in FIG. 9.

According to some embodiments of the present disclosure, by performing one low-pass filtering operation on the generated MinIP image and one high-pass filtering operation on the generated MaxIP image, the low-frequency image and the high-frequency image used to generate the target image may be obtained, which reduces the count of filtering operations (compared to an image processing algorithm including performing filtering operations on each slice image of the batch of slice images), thereby simplifying the image generation process, reducing image processing time, and improving image generation efficiency.

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140 may generate multiple target images correcting to different batches of slice images. Each target image may correspond to a slab of the subject.

Merely by way of example, the processing device 140 may divide the plurality of slice images into different batches according to a division rule. The division rule may include a batch count and an amount of slice images in each batch. In some embodiments, different batches of slice images may include the same or different counts of slice images. In some embodiments, a same slice image may be assigned to two batches of slice images. That is, the corresponding two slabs of the subject represented in two batches of slice images may include an overlapping portion of the subject. For example, the plurality of slice images may be arranged according to their corresponding slice locations, batch 1 may include slice image 1 to slice image 8, batch 2 may include slice image 9 to slice image 20, batch 3 may include slice image 18 to slice image 28, and batch 4 may include slice image 29 to slice image 39. The processing device 140 may generate a target image based on a corresponding batch of slice images according to a similar manner as described in the process 800, thereby allowing preservation, in one target image, of morphological information and information regarding a high attenuation substance within a slab of the subject represented in a batch of slice images. Accordingly, a user may learn information represented in multiple slice images by reviewing corresponding target image(s) to make a diagnosis, thereby obviating the need for the user to review each slice image of the multiple slice images, which in turn may allow the user to improve diagnosis efficiency. In some embodiments, the user may make a diagnosis based solely on the target image(s). In some embodiments, the user may identify, by reviewing target image(s), a slab of the subject that needs to be reviewed more closely, and review the slice images corresponding to a particular target image or the identified slab of the subject to make a diagnosis.

Figure 9:
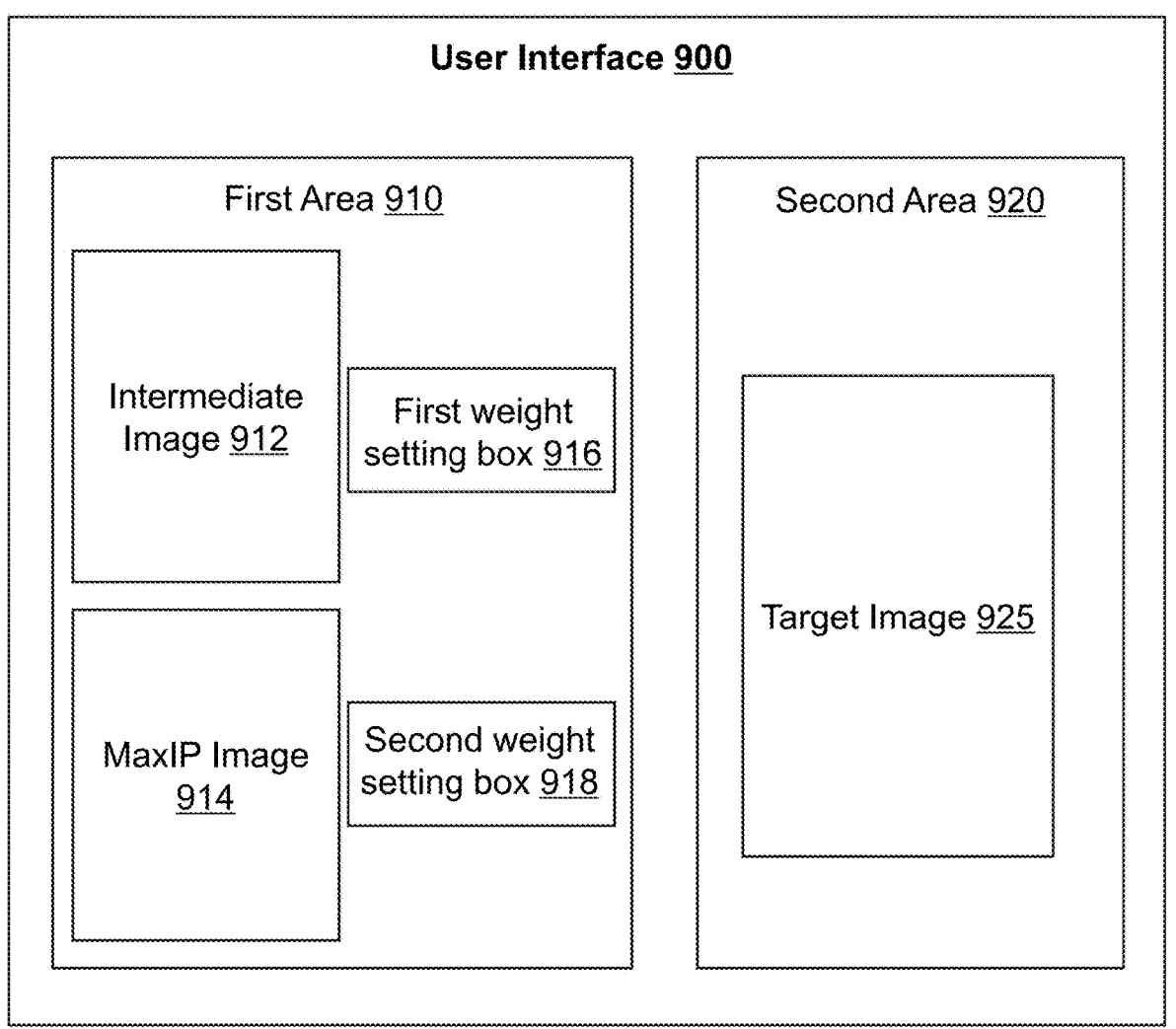
FIG. 9 is a schematic diagram illustrating an exemplary user interface for setting weights to generate a target image according to some embodiments of the present disclosure.

FIG. 9 is a schematic diagram illustrating an exemplary user interface for setting weights to generate a target image according to some embodiments of the present disclosure. As shown in FIG. 9, a user interface 900 may include a first area 910 and a second area 920. The first area 910 may be configured to display an intermediate image 912 and a MaxIP image 914. The first area 910 may also display a first weight setting box 916 and a second weight setting box 918. The second area 920 may be configured to display a target image 925. A user (e.g., a doctor) may input the first weight in the first weight setting box 916 and/or a second weight in the second weight setting box 918. For example, the user may directly input the first weight and/or the second weight by typing on a keyboard. As another example, the user may input the first weight and/or the second weight by selecting a corresponding weight value from candidate weight values provided in a drop-down box. In some embodiments, since a sum of the first weight and the second weight is 1, once one of the first weight and the second weight is inputted, the other one of the first weight and the second weight may be determined automatically. The processing device 140 may generate a target image and cause the target image to be displayed in the second area 920. In some embodiments, the user may adjust the first weight or the second weight according to the displayed target image. The processing device 140 may update the target image displayed in the second area 920, e.g., in real time.

FIG. 10A illustrates an exemplary slice image of a subject. FIG. 10B illustrates an exemplary target image of a slab of a subject according to some embodiments of the present disclosure. As shown in FIGS. 10A and 10B, both the slice image 1000*a* and the target image 1000*b* may include image information of calcification. The target image 1000*b* may include image information of the calcification of multiple slice images. By generating the target image 1000*b* and displaying the target image 1000*b* to a user, instead of the multiple slice images, the user may learn information represented in the multiple slice images by reviewing the target image 1000*b* to make a diagnosis, thereby obviating the need for the user to review each slice image of the multiple slice images, which in turn may allow the user to improve diagnosis efficiency.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

What is claimed is:

1. A system, comprising:

at least one storage device storing executable instructions for image processing; and at least one processor in communication with the at least one storage device, wherein when executing the executable instructions, the at least one processor is configured to cause the system to perform operations including:

obtaining multiple projection images of a subject acquired by an imaging device from multiple view angles, each of the multiple projection images being a two-dimensional projection image acquired by the imaging device from one of the view angles;

generating an initial slice image of the subject corresponding to an initial slice location of the subject by image reconstruction based on the multiple projection images;

determining, based on the multiple projection images, a target out-of-plane artifact of the initial slice image, the target out-of-plane artifact being an image artifact caused by one or more substances outside the initial slice location; and generating a corrected slice image by correcting the initial slice image with respect to the target out-of-plane artifact.

2. The system of claim 1, wherein the at least one processor is further configured to cause the system to perform the operations including:

generating, based on each of the multiple projection images, a back-projection image corresponding to the projection image using a back-projection algorithm.

3. The system of claim 2, wherein the generating, based on each of the multiple projection images, a back-projection image corresponding to the projection image includes:

performing a preprocessing operation on the projection image to generate a preprocessed image, the preprocessing operation including at least one of a segmentation operation, a gray value transformation operation, or a window width adjustment operation, or a window level adjustment operation; and generating, based on the preprocessed projection image, the back-projection image.

4. The system of claim 3, wherein the generating an initial slice image of the subject by image reconstruction based on the multiple projection images includes:

generating, based on the multiple back-projection images, the initial slice image.

5. The system of claim 2, wherein the determining, based on the multiple projection images, a target out-of-plane artifact of the initial slice image includes:

determining an out-of-plane artifact of each back-projection image of the multiple back-projection images; and determining the target out-of-plane artifact based on the multiple out-of-plane artifacts of the multiple back-projection images.

6. The system of claim 5, wherein the determining an out-of-plane artifact of each back-projection image of the multiple back-projection images includes:

determining a residual image between the back-projection image and the remaining back-projection images among the multiple back-projection images; and determining, based on the residual image and the back-projection image, the out-of-plane artifact of the back-projection image.

7. The system of claim 6, wherein the determining a residual image between the back-projection image and the remaining back-projection images among the multiple back-projection images includes:

determining an average back-projection image of the remaining back-projection images among the multiple back-projection images; and determining the residual image by subtracting the back-projection image from the average back-projection image.

8. The system of claim 6, wherein the determining, based on the residual image and the back-projection image, the out-of-plane artifact of the back-projection image includes:

determining, based on a minimum pixel value of pixel values of the residual image corresponding to the back-projection image, a correction weight image; and determining, based on the correction weight image and the back-projection image, the out-of-plane artifact of the back-projection image.

9. The system of claim 5, wherein the determining the target out-of-plane artifact based on the multiple out-of-plane artifacts of the multiple back-projection images includes:

determining the target out-of-plane artifact by summing the multiple out-of-plane artifacts of the multiple back-projection images.

10. The system of claim 1, wherein the generating a corrected slice image by correcting the initial slice image with respect to the target out-of-plane artifact includes:

generating the corrected slice image by subtracting the target out-of-plane artifact from the initial slice image.

11. The system of claim 1, wherein the at least one processor is further configured to cause the system to perform the operations including:

generating, based on the multiple projection images, a plurality of initial slice images of the subject, each of the plurality of initial slice images corresponding to a slice of the subject;

generating a plurality of corrected slice images by correcting the plurality of initial slice images with respect to a plurality of target out-of-plane artifacts;

generating, based on a batch of corrected slice images of the plurality of corrected slice images, a minimum intensity projection (MinIP) image and a maximum intensity projection (MaxIP) image, the batch of corrected slice images corresponding to a slab of the subject;

generating a low-frequency image and a high-frequency image by performing a filtering operation on the MinIP image and the MaxIP image, respectively; and generating, based on the low-frequency image and the high-frequency image, a target image of the slab of the subject.

12. The system of claim 11, wherein the determining, based on a batch of corrected slice images of the plurality of corrected slice images, a minimum intensity projection (MinIP) image and a maximum intensity projection (MaxIP) image includes:

generating the MinIP image by performing an MinIP operation on the batch of corrected slice images; and generating the MaxIP image by performing an MaxIP operation on the batch of corrected slice images.

13. The system of claim 11, wherein the generating a low-frequency image and a high-frequency image by performing a filtering operation on the MinIP image and the MaxIP image, respectively, includes:

determining the low-frequency image by performing a low-pass filtering operation on the MinIP image; and determining the high-frequency image by performing a high-pass filtering operation on the MaxIP image.

14. The system of claim 13, wherein the generating, based on the low-frequency image and the high-frequency image, a target image of the subject includes:

generating an intermediate image by superimposing the low-frequency image and the high-frequency image; and generating, based on the intermediate image and the MaxIP image, the target image.

15. The system of claim 14, wherein the generating, based on the intermediate image and the MaxIP image, the target image includes:

determining a first weight for the intermediate image;

determining a second weight for the MaxIP image; and generating the target image by determining a weighted sum of the intermediate image and the MaxIP image.

16. The system of claim 11, wherein the at least one processor is further configured to cause the system to perform the operations including:

transmitting the target image to a terminal device for display.

17. The system of claim 11, wherein the batch of corrected slice images correspond to consecutive slices of the subject.

18. The system of claim 1, wherein the subject includes a breast, and the imaging device includes a digital breast tomosynthesis (DBT) device.

19. A method for image processing, implemented on a computing device having at least one processor and at least one storage device, the method comprising:

obtaining multiple projection images of a subject acquired by an imaging device from multiple view angles, each of the multiple projection images being a two-dimensional projection image acquired by the imaging device from one of the view angles;

generating an initial slice image of the subject corresponding to an initial slice location of the subject by image reconstruction based on the multiple projection images;

determining, based on the multiple projection images, a target out-of-plane artifact of the initial slice image, the target out-of-plane artifact being an image artifact caused by one or more substances outside the initial slice location; and generating a corrected slice image by correcting the initial slice image with respect to the target out-of-plane artifact.

20. A non-transitory computer readable medium, comprising at least one set of instructions for image processing, wherein when executed by at least one processor of a computing device, the at least one set of instructions direct the at least one processor to perform operations including:

obtaining multiple projection images of a subject acquired by an imaging device from multiple view angles;

for each of the multiple projection images, performing a preprocessing operation on the projection image to generate a preprocessed image, the preprocessing operation including at least one of a segmentation operation, a gray value transformation operation, or a window width adjustment operation, or a window level adjustment operation;

generating, based on the preprocessed projection images of the multiple projection images, back-projection images;

generating an initial slice image of the subject by image reconstruction based on the back-projection images;

determining, based on the multiple projection images, a target out-of-plane artifact of the initial slice image; and generating a corrected slice image by correcting the initial slice image with respect to the target out-of-plane artifact.

\* \* \* \* \*